United States Patent [19]

Campbell

[11] Patent Number: 5,391,372

[45] Date of Patent: Feb. 21, 1995

[54] METHODS OF TREATING COLIC AND FOUNDER IN HORSES

[76] Inventor: Elizabeth Campbell, 7842 S. Marshall Ct., Littleton, Colo. 80123

[21] Appl. No.: 82,553

[22] Filed: Jun. 28, 1993

[51] Int. Cl.$^6$ .............................................. C08G 63/02
[52] U.S. Cl. ................. 424/195.1; 424/196.1; 424/438; 424/439; 424/442
[58] Field of Search .................. 424/195.1, 196.1, 438, 424/439, 442

[56] References Cited

U.S. PATENT DOCUMENTS

| | | | |
|---|---|---|---|
| 1,658,719 | 2/1929 | Hardy | 424/195 |
| 4,352,796 | 10/1982 | Arichi et al. | 424/195 |
| 4,515,785 | 5/1985 | Shimizu et al. | 424/195.1 |
| 4,683,140 | 7/1987 | Kang | 426/597 |
| 4,847,095 | 7/1989 | Alley et al. | 426/74 |

OTHER PUBLICATIONS

"Pine Tar", *National Formulary XIV*, p. 578, published by American Pharmaceutical Association, Jul. 1, 1975.
"Pine Needle Oil", *National Formulary XIV*, p. 820, published by American Pharmaceutical Association, Jul. 1, 1975.
"Pumilio Pine Oil", *Extra Pharmacopoeia*, p. 862, published by The Pharmaceutical Press, 1969.
"Tars with Creosote and Guaiacols", *Extra Pharmacopoeia*, pp. 1420–1421, published by The Pharmaceutical Press, London, 1969.
"Pine Tar", *The United States Dispensory*, 27th ed., p. 1141, published by J. B. Lippincott Co., Philadelphia, Pa., 1973.
Advertisement for "Stom-Ach", item P, p. 56.

*Primary Examiner*—John Kight, III
*Assistant Examiner*—Richard Jones
*Attorney, Agent, or Firm*—Leydig, Boit & Mayer, Ltd.

[57] ABSTRACT

A method of treatment for the relieving of the symptoms of colic in horses is disclosed which comprises orally administering an effective amount of a pine tea which is prepared by boiling pine needles in water to the horse. Suitable pine needles include Ponderosa pine needles.

10 Claims, No Drawings

METHODS OF TREATING COLIC AND FOUNDER IN HORSES

FIELD OF THE INVENTION

The present invention relates generally to a method of treatment of colic and/or founder in horses and more particularly to a method of treatment of administering an effective amount of pine tea to a horse to relieve the symptoms of colic and/or founder.

BACKGROUND OF THE INVENTION

The most common reason for horse death or euthanasia is colic. Of all of the horses affected by colic the death rate from this type of intestinal problem has been reported to be approximately one in ten horses. Colic or symptoms indicating colic may occur within a few hours after feeding. Acknowledged symptoms indicative of colic include refusing grain and hay, kicking at the belly, lying down and getting up only to go down again, attempting to roll with tack on, pawing, kicking out behind, sweating, bloating, looking at the belly, squatting, squealing, and straining as if trying to pass urine.

Two recognized types of colic are tympanic or gas colic and impaction colic. Tympanic or gas colic is caused by excess gas accumulation in the stomach or other portions of the digestive tract. Impaction colic is caused by blockage of the gut, usually the large intestine by ingesta. Colic may often lead to obstruction of the blood supply to the intestine which also is a cause of some of the colic symptoms.

The true causes of gas colic and impaction colic have not been firmly established despite intensive research since its existence was first reported as occurring in an army camp in Scotland at the turn of the century. Current opinion favors the hypothesis that colic is caused by a toxin in the grass or other feed, which damages the nerves of the sympathetic system supplying the gut, causing paralysis of the alimentary tract of the horse. Stress, as well as overfeeding, abnormal feeding schedules or changes in feed, moldy feed, weather changes, cribbing, or ingesting of foreign material may also result in a horse having a colic condition. Gas colic may be caused by the feeding of certain grains to horses which leads to fermentation in the horse's stomach. Ground barley has been found to lead to such fermentation.

The severity and duration of colic in horses depends upon the extent of the damage to the horse's digestive track. In some cases, the colic may resolve itself, but in others it may lead to profound disturbances in fluid and salt content of the blood of the horse and culminate in a state of shock and heart failure causing the death of the horse. Occasionally, severe gas colic may result in a horse suffering a ruptured stomach.

Treatment of colic in the past has included the use of a stomach tube to relieve gas pressure on the horse's stomach and giving an antacid-antigas type medication such as MAALOX™. Also, a common laxative usually given by a veterinarian for a horse showing colic symptoms is a mineral oil administered by stomach tube, which is administered to loosen the blockage. A side effect of giving mineral oil internally to a horse is that the oil will deplete stored vitamins in the horse's system and will also block absorption of vitamins from the horse's stomach.

Another horse ailment often linked to the feeding of horses is founder, also known as acute laminitis. Founder affects the sensitive laminae, the living glue between the horse's coffin bone and the overlying hoof wall. The sensitive laminae of the horse has a circulatory system that normally consists of arteries and veins connected by capillaries. These capillaries around the coffin bone provide oxygen and nutrients to all the parts of the sensitive laminae which are dependent on the continuing supply of blood for their survival. Interruption of this circulation for any reason quickly leads to the death of the sensitive laminae. This condition can necessitate euthanasia of the horse or can result in a chronically unsound horse.

Founder in a horse is a metabolic problem which can be caused by many systemic illnesses among which are colic, respiratory infections or other respiratory ailments, and overwork. Toxins in feed, particularly toxic products of fermenting foodstuffs, and feeding on excessive amounts of grain, especially grain meant for chickens, hogs, and cattle too much grain both may lead to founder in horses. Founder has generally been treated by standing a horse in cold water. Also, anti-inflammatory drugs may be administered in conjunction with a pain killer, and a laxative may be administered to evacuated the toxins from the horse's digestive tract.

A product which has been used in the treatment of various ailments in humans is an oil extracted from pine trees. Such an oil is known under the general name of pine oil or pine needle oil. Such as oil has been described in *Extra Pharmacopoeia*, The Pharmaceutical Press, Edited by Todd, R. G., London, England, 1969, as a colorless or faintly yellow oil with a pleasant aromatic odor and a bitter pungent taste, obtained by distillation from the fresh leaves of the Pinus mugo variety pumilio (Fam. Pinaceae), a variety of mountain pine. Such a pine oil is described as containing about 4% to 10% by weight of esters, calculated as bornyl acetate, $C_{12}H_{20}O_2$.

Oleum Pini Sylvestris or fir-wool oil has also been previously described as an oil distilled from the fresh leaves of the Scotch pine, Pinus sylvestris. Such a pine oil is now available commercially. However, the presently commercially available oil now sold under this name is a distillate from the leaves and twigs of various conifers.

Human usage of such pine oil has taken advantage of pine oil's antiseptic and expectorant properties, as well as its diuretic and laxative properties. Humans have also inhaled the oil mixed with steam, sometimes with the addition of menthol, eucalyptus oil, and compound benzoin tincture, to relieve cough in chronic bronchitis and asthma. Humans have also applied the oil externally to the skin as a rubefacient in the treatment of sprains and fibrositis.

Generally, the buds found at the tips of the shoots of the pine, and the leaves or needles of the pine have been of pharmacological interest in treating humans. The buds were gathered in March or in the autumn when they contain an essential oil with anti-catarrhal and diuretic properties. An infusion of the buds in boiling water, sweetened, has been used to treat human bronchial and bladder infections. Water distilled from the buds has been reported to have similar properties for use in treating humans.

The leaves or needles of the pine tree have been gathered during the summer and a decoction has previously been used in the treatment of rheumatism and gout in humans. The oleo-resin which drains from the bark of the pine tree is used to obtain turpentine, which is then distilled to produce oil of turpentine, which has been used by humans as an antiseptic and a nerve stimulant. Also, the Swiss mountain pine is known to produce pine essence, an essential oil obtained by distillation of the young branches and the buds. This pine essence has been used in the manufacture of bath salts and oils for humans and as an antiseptic and decongestant when taken internally by humans.

The Scots pine produces large quantities of turpentine for commercial use and pharmaceutical use. Its roots are a source of tar which has been found to be very efficacious for treatment of some skin diseases in humans. In the United States a syrup of tar used for scrofulous diseases in humans enjoys a high reputation. Colophony is an oleo-resin which is distilled to extract turpentine. The residue, after distillation, is used in pharmacy to make ointments, liniments and plasters for humans When a pine oil is prescribed for human use, it is most often prescribed as Compound White Pine Syrup, or, Syrupus Pini Albae Compositus. This is, in reality, a herbal mixture and contains several active ingredients. Compound White Pine Syrup is used as a stimulant, aromatic, astringent, or a diuretic. Overdoses have been reported to cause bloating and flatulence and very large overdoses have even caused spasms and convulsions. Compound White Pine Syrup, as used to treat humans, is reported to stimulate both the heart and respiration, and its diuretic action, by increasing the flow of urine, may help the body to rid itself of toxins.

Given the extreme danger of colic to horses, it is an object of the present invention to provide a method of treatment for horses which relieves the symptoms of colic.

Given the extreme danger of founder to horses, it is a further objective of the present invention is to provide a method of treatment of horses which relieves the symptoms of founder.

A third objective of the present invention is to provide a method of treatment of horses which is useful for the treatment of both colic and founder.

Still another objective of the present invention is to provide a safe and effective treatment for colic and/or founder in horses which may be safely administered to a horse by a lay person without the assistance and direction of a veterinarian.

SUMMARY OF THE INVENTION

The present invention relates to a method of treatment for the relieving of the symptoms of colic in horses. A method for treating colic in horses comprising orally administering an effective amount of pine tea to the horse is disclosed. Generally, the pine tea is orally administered by syringe. The pine tea used in the method of treatment is prepared by boiling fresh pine needles in water. These pine needles, which may be Ponderosa pine needles, may be finely chopped. The pine needles are boiled in water for ten minutes. Generally, an effective amount of pine tea is about 5 cubic centimeters per 100 pounds of weight of the horse to be treated. Therefore, for most horses, about 40 to 95 cubic centimeters of pine tea may be administered according to the method.

The present invention further relates to a method of treatment for the relieving of the symptoms of founder in horses. A method for treating founder in horses comprising orally administering an effective amount of pine tea to the horse is disclosed. Generally, the pine tea is orally administered by syringe. The pine tea used in the method of treatment is prepared by boiling fresh pine needles in water. These pine needles, which may be Ponderosa pine needles, may be finely chopped. The pine needles are boiled in water for ten minutes. Generally, an effective amount of pine tea would be about 5 cubic centimeters per 100 pounds of weight of the horse to be treated. Therefore, for most horses, about 40 to 95 cubic centimeters of pine tea may be administered according to the method.

Also disclosed is a method of treatment for the relieving of the symptoms of colic and founder in horses. The method comprises orally administering an effective amount of pine tea to the horse. Generally, the pine tea is orally administered by syringe. The pine tea used in the method of treatment is prepared by boiling fresh pine needles in water. These pine needles, which may be Ponderosa pine needles, may be finely chopped. The pine needles are boiled in water for ten minutes. Generally, an effective amount of pine tea would be about 5 cubic centimeters per 100 pounds of weight of the horse to be treated. Therefore, for most horses, about 40 to 95 cubic centimeters of pine tea may be administered according to the method.

DETAILED DESCRIPTION OF THE INVENTION

The present invention relates to a method of treatment for the relieving of the symptoms of colic in horses comprising orally administering an effective amount of pine tea to the horse is disclosed. The pine tea used in the method of the invention preferably does not contain a sedative or a painkiller. A pine tea for use in the method of the invention may be prepared by boiling pine needles in water and then straining the needles from the pine tea. Preferably, four ounces of fresh pine needles are boiled in one pint boiling water.

Also, the pine needles are preferably from a Ponderosa pine and are finely chopped. The pine needles are preferably steeped in boiling water for ten minutes during the boiling process. The pine tea produced by this procedure is very high in vitamin C, approximately five times higher than the juice of a lemon. The pine tea, prepared in such a manner is also high in vitamin A, a known stimulant.

The pine tea, prepared in such a manner is also an excellent laxative for horses. Such a pine tea also stimulates both heart and respiration of a horse. The diuretic effect of such a pine tea on a horse increases the flow of urine which in turn rids the body of the horse of toxins.

To relieve the symptoms associated with colic, an effective amount of the strained pine tea prepared in the manner described above is orally administered to a horse, preferably using a syringe. The pine tea may also be administered as distilled concentrated liquid or mixed in a molasses base, or other inert paste that makes the tea a more palatable consistence for a horse.

Preferably, from about 40 to about 95 cubic centimeters of pine tea prepared in the manner described above, more preferably about 60 cubic centimeters, are orally administered to an adult horse weighing approximately 1200 pounds. An appropriate ratio may be used in calculating a most preferred amount of pine tea for horses weighing less than or greater than 1200 pounds at the rate of 5 cubic centimeters per 100 pounds of weight. Administered orally to a horse, the above described pine tea will stimulate a horse's blood flow and act as a diuretic and a laxative.

The described method of treatment using pine tea is a safe and effective method of treatment of colic symptoms in a horse for use by a lay person. Further, the tea provides valuable minerals to the horse. Also, the described method of treatment is considerably less expensive than veterinarian administered treatments presently in use.

After orally administering an effective amount of the pine tea, the horse is preferably hand walked for about 10 minutes. Typically about ten minutes after orally administering an effective amount of pine tea to a horse, the horse will pass stool and gas, thereby relieving the symptoms of colic.

The present invention further relates to a method of treating founder in horses comprising orally administering an effective amount of pine tea to the horse is disclosed. Orally administering pine tea in an effective amount will increase a horse's circulation to remove toxic products & edema from laminar area. The pine tea's laxative effect assists in evacuating toxins from the horse's stomach which the diuretic action of the pine tea is helpful in reducing congestion in the horse's feet, thereby increasing the horse's metabolism which will aid in the horse's recovery.

A pine tea for use in the method for treating the symptoms of founder may be prepared by boiling pine needles in water and then straining the needles from the pine tea. Preferably, four ounces of fresh pine needles are boiled in one pint boiling water. Also, the pine needles are preferably from a Ponderosa pine and are finely chopped. The pine needles are preferably steeped in boiling water for ten minutes during the boiling process.

The pine tea, prepared in such a manner is an excellent laxative for horses. Such a pine tea also stimulates both heart and respiration of a horse. The diuretic effect of such a pine tea on a horse increases the flow of urine which in turn rids the body of the horse of toxins.

To relieve the symptoms associated with founder, an effective amount of the strained pine tea prepared in the manner described above is orally administered to a horse, preferably using a syringe. The pine tea may also be administered as distilled concentrated liquid or mixed in a molasses base, or other inert paste that makes the tea a more palatable consistence for a horse. Preferably, from about 40 to about 95 cubic centimeters of strained pine tea prepared in the manner described above, more preferably about 60 cubic centimeters, are orally administered to an adult horse weighing approximately 1200 pounds. An appropriate ratio may be used in calculating a most preferred amount of pine tea for horses weighing less than or greater than 1200 pounds at the rate of 5 cubic centimeters per 100 pounds of weight. Administered orally to a horse, the above described pine tea will stimulate a horse's blood flow and act as a diuretic and a laxative.

The described method of treatment using pine tea is a safe and effective method of treatment of founder symptoms in a horse for use by a lay person. Further, the tea provides valuable minerals to the horse. Also, the described method of treatment is considerably less expensive than veterinarian administered treatments presently in use.

After orally administering an effective amount of the pine tea, the horse may be hand walked for about 10 minutes. Also, the horse's affected legs may be place in cold water or wrapped in towels soaked in cold water. Typically about ten minutes after orally administering an effective amount of pine tea to a horse, the horse will pass stool and gas, thereby relieving the symptoms of colic.

Readily seen from the above description is that a simple treatment for both colic and founder has been discovered. Therefore, the present invention further relates to a method of treating founder and/or colic in horses comprising orally administering an effective amount of pine tea to the horse is disclosed. A pine tea for use in the method for treating the symptoms of founder may be prepared by boiling pine needles in water and then straining the needles from the pine tea. Preferably, four ounces of fresh pine needles are boiled in one pint boiling water. Also, the pine needles are preferably from a Ponderosa pine and are finely chopped. The pine needles are preferably steeped in boiling water for ten minutes during the boiling process.

To relieve the symptoms associated with founder and/or colic, an effective amount of the strained pine tea prepared in the manner described above is orally administered to a horse, preferably using a syringe. The pine tea may also be administered as distilled concentrated liquid or mixed in a molasses base, or other inert paste that makes the tea a more palatable consistence for a horse. Preferably, from about 40 to about 95 cubic centimeters of strained pine tea prepared in the manner described above, more preferably about 60 cubic centimeters, are orally administered to an adult horse weighing approximately 1200 pounds. An appropriate ratio may be used in calculating a most preferred amount of pine tea for horses weighing less than or greater than 1200 pounds at the rate of 5 cubic centimeters per 100 pounds of weight.

The described method of treatment using pine tea is a safe and effective method of treatment of founder and/or colic symptoms in a horse for use by a lay person. Further, the tea provides valuable minerals to the horse. Also, the described method of treatment is considerably less expensive than veterinarian administered treatments presently in use.

After orally administering an effective amount of the pine tea, the horse is preferably hand walked for about 10 minutes. Where founder is suspected, the horse's affected legs may be place in cold water or wrapped in towels soaked in cold water. Typically about ten minutes after orally administering an effective amount of pine tea to a horse, the horse will pass stool and gas, thereby relieving any symptoms of colic and ridding its system of toxins which lead to symptoms of founder.

The following are examples of the use of the methods of the inventions.

Example 1

A thoroughbred gelding foaled in 1984 exhibited colic symptoms. At 4:30 p.m., the horse was grazing for about 1 hour. Although the horse appeared hungry, he also appeared distressed. He was also rolling about next to a fence. The horse was placed in an arena and a pine tea was prepared. The pine tea was prepared by boiling four ounces of finely chopped Ponderosa pine needles in one pint of water for approximately ten minutes and the needles were then strained from the pine tea. Sixty cubic centimeters of pine tea were then administered orally to the horse using a syringe. Of the sixty cubic centimeters administered, 40 cubic centimeters were actually ingested by the horse. Within a few minutes, the horse passed excessive amounts of gas and almost immediately exhibited healthy, non-colic signs. By 6:00 p.m., the horse was eating his hay in his stall. By 7:30 p.m., the horse had passed two piles of soft manure.

Example 2

Three days later, the same thoroughbred gelding described in Example 1 again exhibited colic symptoms. At 1:55 p.m., the horse was in its stall and appeared agitated and wanting to roll. The horse was placed in an outside arena and a pine tea was prepared. The pine tea was prepared by boiling four ounces of finely chopped Ponderosa pine needles in one pint of water for approximately ten minutes and the needles were then strained from the pine tea. 40 cubic centimeters of pine tea were then administered orally to the horse using a syringe. At 2:05 p.m., the horse passed manure and by 2:20 p.m., the horse appeared more relaxed.

At 2:35 p.m., the horse laid down, got up, and started to nibble hay. At 3:00 p.m., the horse was put out in a large pasture area where he again passed manure. The horse then laid down, got up and stretched. At 3:20 p.m., the horse was placed in a stall where he laid down and appeared tired. At 5:00 p.m., the horse was hand walked for ten minutes and the horse appeared in improved condition. At 6:00 p.m. the horse urinated, ate hay and appeared well.

Example 3

An arabian mare foaled in 1984 exhibited colic symptoms. At 1:00 p.m., the horse was lying down in outside arena, looking at her stomach. The horse was placed in a stall where by 2:00 p.m., her condition had worsened. At 2:20 p.m., the horse's temperature was 99.5 F. A pine tea was prepared by boiling four ounces of finely chopped Ponderosa pine needles in one pint of water for approximately ten minutes and the needles were then strained from the pine tea.

Thirty five cubic centimeters of pine tea were then administered orally to the horse using a syringe at 2:23 p.m. At 2:28 p.m. the horse passed gas and at 2:36 p.m., the horse has loose stool. However, the horse continued to lie down and stretch out and the horse appeared tired. At 3:30 p.m., an additional 60 cubic centimeters of pine tea prepared in the manner described previously in the example was administered to the horse. Approximated 5-10 cubic centimeters of this dosage was not swallowed by the horse.

At 3:37 p.m., the horse passed soft stool containing wood pieces, the likely cause of the colic symptoms. At 6:00 p.m., the horse is eating her hay and at 8:30 p.m., the horse appears comfortable, is drinking water and moving about.

From the foregoing description and examples, it is apparent that the objects of the present invention have been achieved. The new method of treatment for colic and/or founder in horses is a safe and effective method of treatment which may be carried out by a lay person without the assistance or direction of a veterinarian.

While only certain embodiments have been set forth, alternative embodiments and various modifications will be apparent to those skilled in the art. These and other alternatives are considered equivalents and within the spirit and scope of the present invention.

What is claimed is:

1. A method of treatment for the relieving of the symptoms of colic in horses, said method comprising orally administering an effective amount of a pine tea prepared by boiling pine needles in water at a ratio of about four ounces of pine needles per one pint of boiling water to the horse sufficient to relieve the symptoms of colic.

2. The method of claim 1, wherein said pine tea is orally administered by syringe.

3. The method of claim 1, wherein said pine tea is prepared by boiling fresh pine needles in water.

4. The method of claim 3, wherein said fresh pine needles are finely chopped.

5. The method of claim 3, wherein said fresh pine needles are boiled for ten minutes.

6. The method of claim 1, wherein said effective amount of pine tea is about 5 cubic centimeters per 100 pounds of weight of the horse to be treated.

7. The method of claim 1, wherein said effective amount of pine tea is from about 40 cubic centimeters to about 95 cubic centimeters.

8. The method of claim 3, wherein said pine needles are Ponderosa pine needles.

9. The method of claim 1, wherein said colic is tympanic colic.

10. The method of claim 1, wherein said colic is impaction colic.

* * * * *